(12) United States Patent
Fischell et al.

(10) Patent No.: US 11,684,520 B1
(45) Date of Patent: Jun. 27, 2023

(54) SYSTEM AND METHOD FOR TREATING NASAL BLEEDING

(71) Applicants: Robert E. Fischell, Dayton, MD (US); Arthur M. Saul, Freehold, NJ (US)

(72) Inventors: Robert E. Fischell, Dayton, MD (US); Arthur M. Saul, Freehold, NJ (US)

(*) Notice: Subject to any disclaimer, the term of this patent is extended or adjusted under 35 U.S.C. 154(b) by 0 days.

(21) Appl. No.: 16/946,695

(22) Filed: Jul. 1, 2020

Related U.S. Application Data

(63) Continuation-in-part of application No. 16/397,062, filed on Apr. 29, 2019, now Pat. No. 10,736,792.

(51) Int. Cl.
| | | |
|---|---|---|
| *A61F 13/20* | (2006.01) | |
| *A61L 15/28* | (2006.01) | |
| *A61L 15/44* | (2006.01) | |
| *A61L 15/20* | (2006.01) | |

(52) U.S. Cl.
CPC .......... *A61F 13/2005* (2013.01); *A61L 15/20* (2013.01); *A61L 15/28* (2013.01); *A61L 15/44* (2013.01); *A61L 2300/232* (2013.01); *A61L 2300/418* (2013.01); *A61L 2300/61* (2013.01)

(58) Field of Classification Search
CPC ........ A61F 13/2005; A61F 5/08; A61F 13/38; A61F 13/126; A61F 13/36; A61F 13/2074; A61F 13/2017; A61F 13/2042; A61F 17/00; A61F 2/82; A61F 2013/00472; A61F 2013/00476; A61M 2210/0618; A61M 35/006; A61M 2210/0681; A61M 15/08; A61B 17/24; A61B 17/12104; A61B 10/02; A61B 2017/246; A61B 10/0045; A45D 40/262; A45D 34/042; A45D 40/265; A45D 40/267; A45D 34/045; A45D 40/264;
(Continued)

(56) References Cited

U.S. PATENT DOCUMENTS 1,573,648 A * 2/1926 Josephh ................ B65D 47/42
D28/88
2,935,186 A * 5/1960 Clark ...................... A61F 17/00
D24/227
(Continued)

FOREIGN PATENT DOCUMENTS

| | | | |
|---|---|---|---|
| CN | 208511703 U | * | 2/2019 |
| JP | 2004041267 A | * | 2/2004 |
| KR | 20210062158 A | * | 11/2019 |

*Primary Examiner* — Adam Marcetich
(74) *Attorney, Agent, or Firm* — Rosenberg, Klein & Lee

(57) ABSTRACT

A blood coagulant assembly includes a blood coagulant device adapted to be insertable into a nostril of a patient to stop a nose bleed. The blood coagulant device is mounted within a blood coagulant device container which has a top container section and a lower container section secured to each other in a releasable manner. The blood coagulant device is mounted in a fixed position within the blood coagulant device container prior to its removal from the blood coagulant container. The blood coagulant device has a rigid handle configured with a handle lower section and a handle upper section contoured with a channel passing through both the lower and upper handle sections. A blood coagulant mechanism is secured to an outer surface of the handle upper section and a to a ledge section of the handle member which extends radially at a joint location of the handle's lower and upper sections.

12 Claims, 3 Drawing Sheets

(58) Field of Classification Search
CPC .......... A45D 2200/1018; A45D 34/046; A45D 40/0087; B01L 3/5029
See application file for complete search history.

(56) References Cited

U.S. PATENT DOCUMENTS

| | | | | |
|---|---|---|---|---|
| 3,586,380 | A * | 6/1971 | Alibeckoff | A61F 13/38 |
| | | | | D24/119 |
| 3,924,623 | A * | 12/1975 | Avery | A61M 35/006 |
| | | | | 604/3 |
| 3,935,859 | A * | 2/1976 | Doyle | A61F 5/05891 |
| | | | | 606/199 |
| 5,895,408 | A * | 4/1999 | Pagan | A61F 13/2005 |
| | | | | 606/162 |
| 7,563,239 | B1 * | 7/2009 | Hudson | A61F 13/38 |
| | | | | 15/244.1 |
| 8,118,511 | B1 * | 2/2012 | Stadnyk | A45D 34/04 |
| | | | | 401/262 |
| 9,943,157 | B1 * | 4/2018 | Chang | A61M 35/006 |
| 2004/0267180 | A1 * | 12/2004 | Beaudry | A61F 13/38 |
| | | | | 604/1 |
| 2005/0019087 | A1 * | 1/2005 | Tsaur | B65D 1/095 |
| | | | | 604/3 |
| 2008/0119776 | A1 * | 5/2008 | Wu | A61F 13/38 |
| | | | | 604/1 |
| 2012/0071913 | A1 * | 3/2012 | Tamez | A61F 5/08 |
| | | | | 606/199 |
| 2013/0012857 | A1 * | 1/2013 | Flynn | A61L 15/28 |
| | | | | 241/24.1 |
| 2019/0029880 | A1 * | 1/2019 | DuBois | A61F 7/03 |
| 2020/0069321 | A1 * | 3/2020 | Zhao | A61B 17/24 |

* cited by examiner

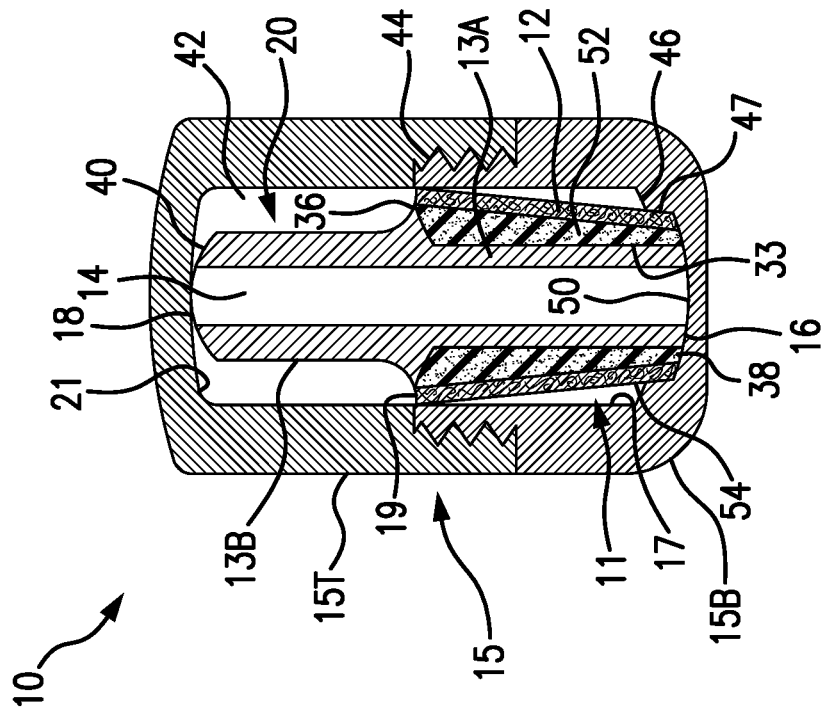
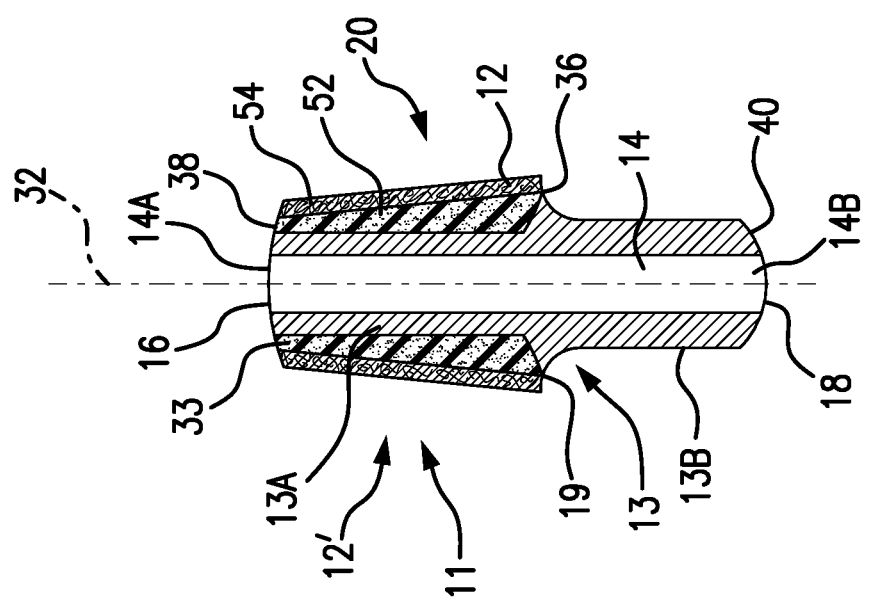

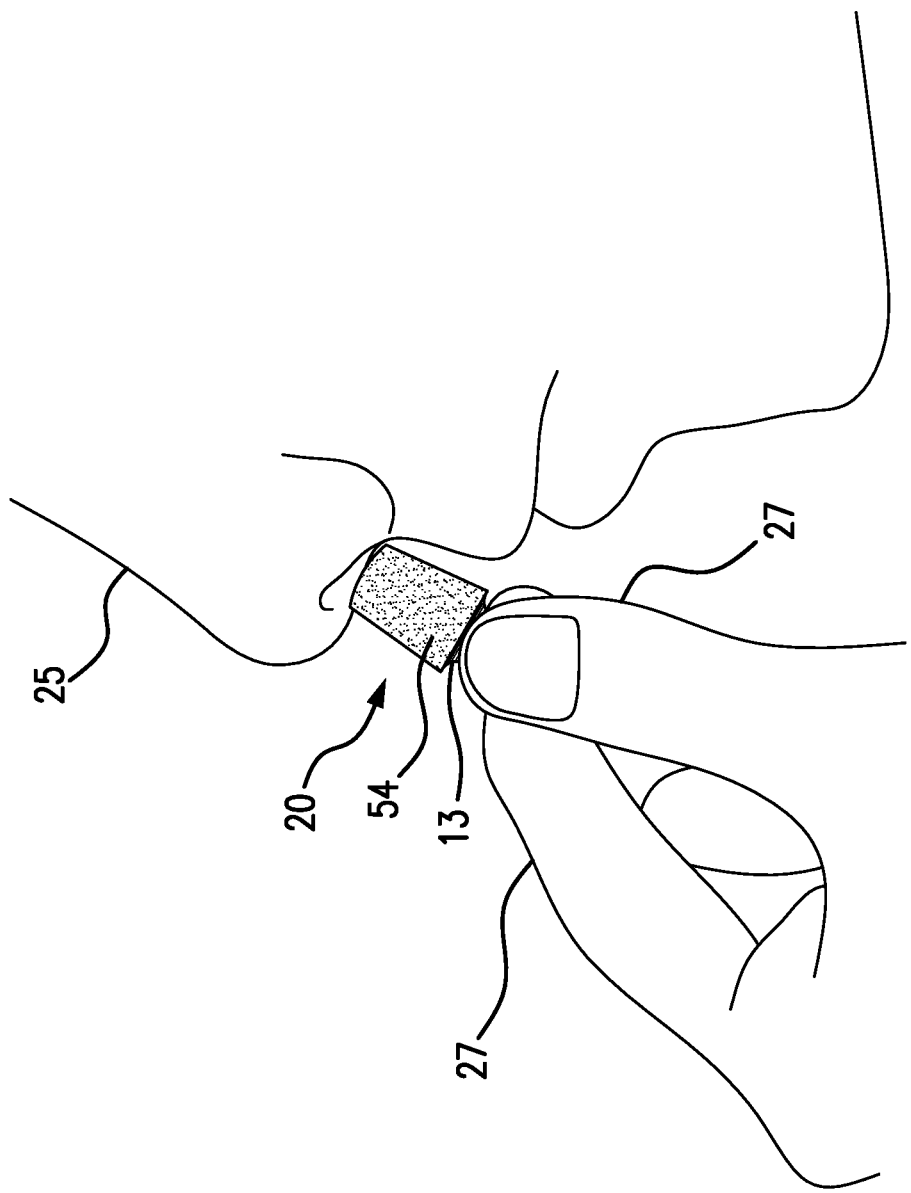

SYSTEM AND METHOD FOR TREATING NASAL BLEEDING

FIELD OF THE INVENTION

The present invention is directed to a treatment of a nosebleed (also known as epistaxis).

In particular, the present invention addresses an effective treatment protocol for nosebleeds, and specifically a nosebleed stopping device and a method of the application of the subject nosebleed stopping device for treatment.

More in particular, the present invention is directed to a nosebleed stopping device and a container for storing the nosebleed stopping device between its usage.

BACKGROUND OF THE INVENTION

Nosebleeds (the episodes of epistaxis) are very common, and, although rarely life threatening, are to be controlled, and, once present, are to be stopped. However, depending on a cause of a nosebleed, such may be difficult to control. That is particularly the case for the patients who are on blood thinners regimen to prevent a stroke.

Numerous medicinal compositions and devices have been applied to stop bleeding. For example, M. B. Dowling, et al., in U.S. Pat. No. 8,932,560, describe a hemostatic tissue sealant sponge and spray for acute wounds. The sponge comprises hydrophobically modified polymers that anchor themselves within the membrane of cells in the vicinity of a wound. The spray comprises hydrophobically modified polymers that form solid gel networks with blood cells to create a physical clotting mechanism to prevent loss of blood. As an example, the '560 Patent uses chitosan that is a natural polysaccharide that is modified with hydrophobic moieties. However, Dowling, et al. is not adapted for nosebleeds stopping. Patients who suffer from severe nasal bleeding are in need for a mechanism to apply chitosan (or some other blood clotting composition) directly to the interior surface of a nostril.

Aluminum chloride-6-hydrate 21.3% (referred to herein as the ACH drug), is described in U.S. Pat. No. 5,702,035. The ACH drug can be used with a Q-Tip for cuts that men occasionally experience when shaving. It is envisioned that such a drug, when placed on the outer surface of a sponge-like-material, would be effective in stopping nose bleeds.

A cylindrically-shaped tampon-like device coated with zinc oxide is described in U.S. Pat. No. 5,584,822 to B. W. Lively, et al. The device presented in the '822 Patent is designed for insertion into a nostril of a nose to stop bleeding. However, the device presented in the '822 Patent does not contemplate storage of the tampon in a container that would be configured for containment of the tampon between its usage, nor does it describe a mechanism which would expel an excess of blood from the nose while the tampon remains in place in the nostril. In addition, the '822 Patent does not provide a coating for the tampon that would promote a healing of the ulceration (or a wound) which is the source of the nasal bleeding.

In U.S. Pat. No. 6,768,040, R. W. Sessions, et al., describe a tapered insert that can be placed into a nostril of a nose to stop bleeding. However, similar to the Lively's '882 Patent, Sessions provide neither for an interior passageway to allow removal of an excess of blood from the nasal cavity, nor is there an efficient way to store the nasal insert within a special container prior to its insertion in the nose. Also, the device described in the '040 Patent does not provide any coating for the tampon-like insert that would be capable of stopping the nosebleed and providing a healing effect directly on the interior surface of the nostril.

In U.S. Patent Application No. 2013/0116656, Yong Song describes a device for stopping nose bleed that is configured with a central opening for draining excessive blood. However, Yong Song provides neither a handle for the device, nor does it describe any blood coagulating coating of the nasal insert. In addition, Yong Song does not provide a container specifically configured for fast and efficient access to the device for quick insertion into the nose. Still further, Song does not describe coating of the tapered end of the nose bleed stopper with a medication that can close the bleeding ulceration inside the nasal cavity and promote the healing of the bleeding ulceration.

SUMMARY OF THE INVENTION

The present invention addresses a device and a method for controlling severe nosebleeds, particularly including patients taking blood thinners as a regimen to preclude the possibility of a stroke that may be caused by atrial fibrillation.

The present device is configured as a nasal insert that is slightly tapered at a top section at the distal end of the device to conveniently slide up into a bleeding nostril and a handle at the proximal section of the device, that is used for both inserting the bleed stopping device into the nostril of interest and removing the device upon the bleeding has been essentially stopped.

The outside tapered surface of the top section of the bleed stopping device is coated with a sponge-like material which is impregnated with a blood clotting composition, such as, for example, chitosan or ACH drug that is brought in contiguous contact with the inner surface of the bleeding nostril in order to clot blood to prevent further bleeding.

It is conceived that the ACH drug has a propensity for healing the bleeding ulceration in the nasal passageway, that eventually results in prevention of recurrences of nose bleeds.

The subject system provides an effective nosebleed stopping treatment, with the time duration of the treatment typically as short as a few minutes to achieve the nosebleed stoppage. Such short treatment time is due to the ability of the chitosan or the ACH drug, or some equivalent bleed stopping drug, to promote the effective blood clotting at the region of the ulceration within the bleeding nostril.

The subject system is configured with a through channel having a comparatively large diameter that extends for the entire length of the device. The through channel serves at least two important functions, namely: (a) it facilitates the passage of the excess blood from the patient's nostril and nasal cavity to an outside of the device, and (b) when the blood flow ceases, the through channel provides an air passage for the patient to breathe even with the subject device remaining in the nostril. The handle at the proximal end of the device is formed from a rigid material (such as, for example, the plastic Lucite). The rigid handle extends from the proximal end of the device into the sponge-like portion at the distal end of the device, thus reinforcing the sponge-like portion to prevent its deformation when in use. The sponge-like portion is impregnated with the blood clotting drug, and when inserted into the nostril, is applied to and presses against the nostril internal surface to clot the blood originating thereat and to heal the ulceration.

It is an object of the present invention to provide a device coated with chitosan or ACH drug, or any other bleed-stopping drug, insertable into a bleeding nostril of a patient's nose in a contiguous contact with the internal surface of the nostril to efficiently clot the blood, thus stopping the nosebleed in a short period of time.

It is another object of the present invention to configure the main body of the device with a sponge-like material which may be impregnated with chitosan, ACH drug, or any other blood clotting composition, to be brought into a contiguous contact with the internal surface of the bleeding nostril for expedited blood stopping.

It is an additional object of the present invention to provide a nosebleed stopping device formed with a handle fabricated of a rigid plastic that extends into the sponge-like material inserted the nostril to serve as a back-bone and to reinforce the sponge-like material for insertion into the nostril, where the rigid handle is designed to be held by the patient's hand for insertion of the nosebleed stopping device into the nostril, and removal of the nosebleed stopping device from the nostril upon the nosebleed has been stopped.

Still another object of the present invention is to provide the nosebleed stopping device configured with an internal channel that extends substantially the entire length of the device (from the distal end to the proximal end) to facilitate the downward outflow of blood from the nostril, and to allow the patient to breathe through the device until it is removed from the patient's nose.

These and other objects and advantages of the present invention will become more apparent to a person of ordinary skill in art upon reading the detailed description in conjunction with the drawings presented herein.

BRIEF DESCRIPTION OF THE DRAWINGS

FIG. 1 is a cross-sectional view of the subject nosebleed stopping device designed for insertion into a nostril to stop nosebleed;

FIG. 2 is a cross-section of the subject nosebleed stopping device stored in a container configured to provide an easy access to the nosebleed stopping device's handle for removal from the container for the treatment usage;

FIG. 4 illustrates the subject nosebleed clotting device inserted into a nostril for controlling the nosebleed.

DETAILED DESCRIPTION OF THE INVENTION

Figure 3:
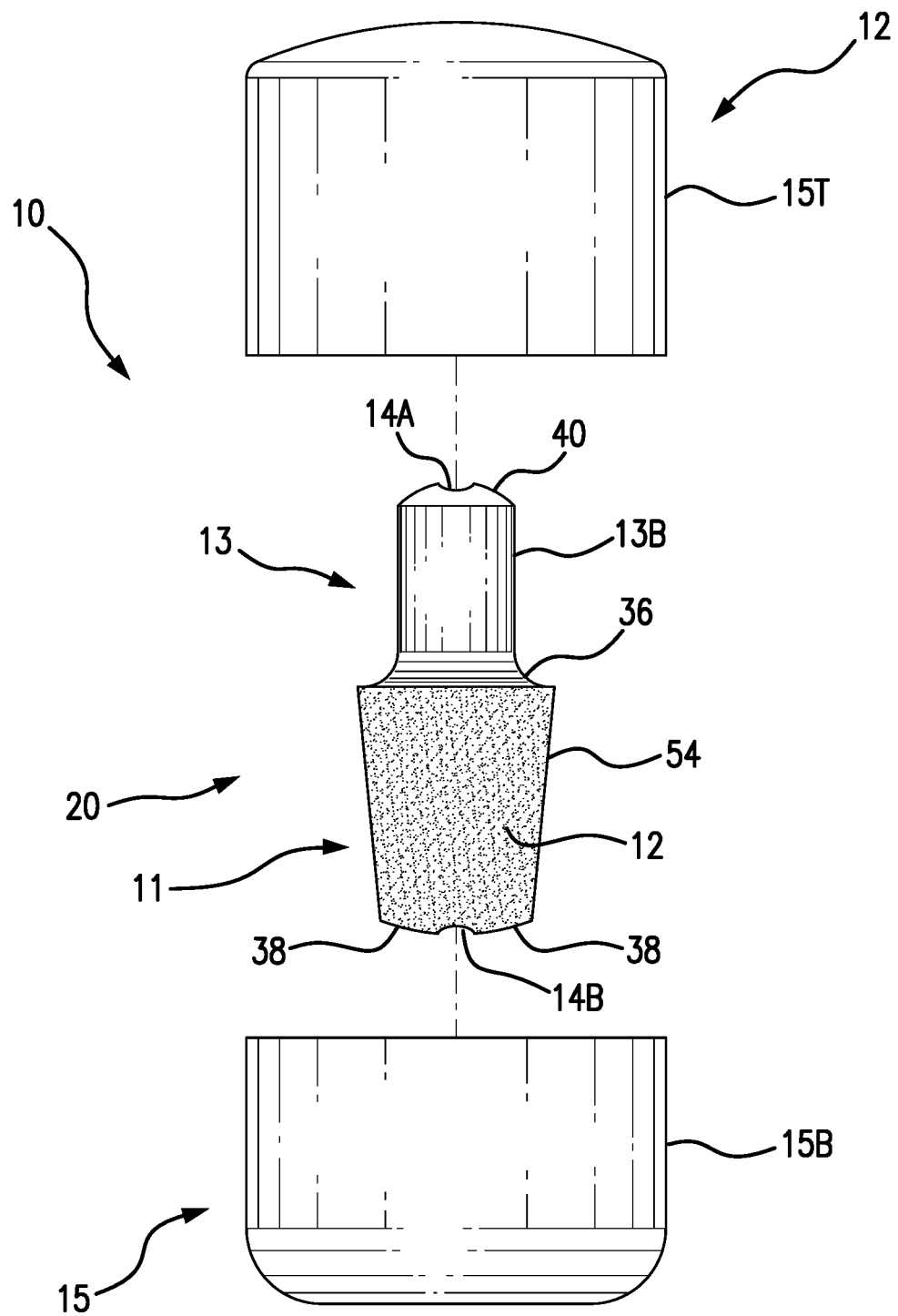
FIG. 3 is an exterior view of the subject assembly containing the nosebleed stopping device as well as the top piece and the bottom piece of the subject container configured to store the nosebleed stopping device.

As shown in FIGS. 1-4, the subject assembly 10 includes a nosebleed stopping device 20 designed for insertion into a patient's nose to stop an episode of a nosebleed. The nosebleed stopping device 20 has a tapered, sponge-like upper portion 11 insertable in a nostril.

The sponge-like portion 11 is impregnated with a blood clotting drug 12 that promotes the nosebleed stoppage 25.

The bleed-stopping drug 12 can either form an outer coating on a surface of the tapered sponge-like upper portion 11, or, alternatively, can impregnate an external layer of a predetermined thickness of the sponge-like material of the tapered sponge-like upper portion 11. The blood clotting drug 12 could be, for example, chitosan, aluminum chloride-6-hydrate 21.3% (ACH drug), or any other comparable medication, and their combination, that can stop bleeding from inside of a patient's nostril.

The ability of the ACH drug to heal an ulcerated and bleeding portion of the internal surface in the nostril is an additional benefit in addition to blood clotting quality, so that the patient can encounter fewer nosebleeds, and possibly, no recurrent episodes of the nosebleed.

The subject device 20 is configured with a handle 13 which extends along the entire length of the device 20. The handle 13 has a distal portion 13A extending within the tapered sponge-like section 11 and a proximal portion 13B which extends downward from the tapered sponge-like section 11 of the device 20. The distal portion 13A of the handle 13 has an outside diameter which is smaller than an outside diameter of the handle 13 at its proximal portion 13B.

A channel 14 extends through the entire length of the handle 13 and terminates, at the distal end 16 of the device 20, in an opening 14A. At the proximal end 18 of the device 20, the channel 14 terminates in an opening 14B.

The channel 14 serves a dual purpose in the subject device 20. One purpose of the channel 14 is to allow for an excess of blood to be expelled out of the nose to an outside of the device 20 when inserted into a nostril to treat the nosebleed. The channel 14 also serves as an air-passage for the patient to breathe through after the device 20 has been inserted into the patient's nose and upon the nosebleed has been stopped.

Due to extension of the channel 14 through the entire length of the device 20, i.e., the length of the distal portion 13A and proximal portion 13B of the handle 13, blood that has flowed into the nasal cavity prior to the insertion of the device 20, can be removed from the nostril to the outside of the device 20 through the channel 14. Once there is no blood remaining to flow through the channel 14, it can be used by the patient to breathe through the channel 14 while the device 20 remains the patient's nostril.

To be applicable to treating nosebleed for various sizes of noses/nostrils, it is contemplated that the device 20 is fabricated in different dimensions of its lengths and diameters. The range of the largest outer diameter of the upper portion 11 is contemplated to vary from ~1.0 cm to as small 0.3 cm to accommodate a very small nostril. The length of the upper portion 11 would be approximately 2 cm with a maximum possible length of 4 cm and a minimum possible length of 1.0 cm.

The taper of the sponge-like upper portion 11 is contemplated to vary from as little as zero degrees to as much as 10 degrees with an optimum taper being approximately 3 degrees.

Although the handle 13 can have a great variety of lengths and diameters, an optimum diameter is envisioned to be about 2 mm smaller than the outer diameter of the flange 36 at the bottom of the upper portion 11 of the handle 13. The length of the proximal portion 13B of the handle 13 may range from ½ cm to as long as 5 cm with an optimum length of 2 cm. The channel 14 that extends through the entire length of the device 10 can have a diameter ranging from as small as 1.0 mm to as large as 7.0 mm with a preferred diameter being approximately 3 mm.

As shown in FIGS. 2 and 3, the subject assembly 10 also includes the bottle (also referred to herein as a container) 15 which is configured to store the nosebleed stopping device 20. The bottle (container) 15 is fabricated with two parts which can be removably attached one to another to form an enclosure 42 configured specifically to enclose the subject device 20. The bottle (container) 15 has a bottom section (portion) 15B and a top section (portion) 15T which may be attached to one another via a threaded engagement 44 or a slide fitting engaging mechanism to form the enclosure 42 for storing the device 20.

An interior surface 17 of the bottom section 15B is contoured to accommodate the tapered portion 11 of the subject device 20. The medicinal composition 12 is placed onto and into the sponge-like tapered upper portion 11. The interior surfaces 17 of the bottom 15B of the container 15 are contoured to remain in close contact with the distal end 16 and the bottom 19 of the tapered portion 11, as shown in FIG. 2 to prevent the device 20 from an unwanted side-wise displacement within the container 15.

A top interior surface 21 of the top section 15T of the container 15 is contoured to remain in close contact with the proximal end 18 of the handle 13 of the device 20. As shown in FIG. 2, the device 20 remains supported in a stable position within the container 15 by the contoured internal surfaces 17 and 21 of the bottom portion 15B and the top portion 15T, respectively, of the container 15.

When a patient (user) experiences a nosebleed, the subject assembly 10 can be used to stop bleeding. With a simple twist (or slide) motion of the top portion 15T and the bottom portion 15B relative one another, the top portion 15T of the container 15 can be disassembled from the bottom portion 15B. Subsequently, while the device 20 remains within the bottom portion 15B of the container 15 (the bottom portion 15B being held in one of the user's hands), the user engages the handle 13 of the nosebleed stopping device 20 and removes the device 20 from the bottom portion 15B of the container 15. The device 20 removed from the container 15 is subsequently placed with its tapered upper portion 11 into that patient's nostril to stop the bleeding.

FIG. 3 depicts an exterior view of the nosebleed stopping device 20 prior to its insertion into the bottom section (portion) 15B of the container 15 and prior to securing the section 15T to the bottom section (portion) 15B.

FIG. 4 illustrates the subject device 20 placed by the user into a nostril of the user's nose 25. The user holds the handle 13 (obscured in FIG. 4) of the device 20 by the fingers 27 to place the device 20 into the nose 25 to stop the bleeding.

In particular, to further clarify the inventive concept of the subject matter, FIGS. 1-4 are directed to a blood coagulant assembly 10 (best shown in FIGS. 2 and 3) which includes the nosebleed device (also referred to herein as a blood coagulant device) 20 shown in FIGS. 1-4. The blood coagulant device 20 is adapted to be reversibly insertable into a nostril of the nose 25 of a patient experiencing a nose bleed and a blood coagulant device container 15 having a container top section (also referred to herein intermittently as a container top portion) 15T and a container lower (bottom) section (also referred to herein intermittently as a portion) 15B. When the blood coagulant device 20 is stored in the blood coagulant container 15, the container lower section 15B and the container top section 15T are secured each to the other in a releasable manner for housing (or containing) the blood coagulant device 20 in a fixed location and in a stable position within the blood coagulant device container 15 prior to the removal of the blood coagulant device 20 from the blood coagulant container 15. Positioning and maintaining the blood coagulant device 20 in a fixed location within the blood coagulant container 15 is an important aspect of the subject assembly 10 due to the fact that the coagulant layer 54 of the blood clotting device 20 may be somewhat fragile in nature and can be eroded when the blood coagulant container 15 (with the blood coagulant device 20 stored therein) is displaced, thereby reducing the effectiveness of the blood coagulant device 20 when in use.

Thus, it is important that when the blood coagulant device 20 is stored in the blood coagulant container 15 for extended periods of time and subject to varying displacements of the container 15, that a minimum surface area of the coagulant layer 54 interface with the internal surfaces 17, 21 of the container 15 while maintaining the blood coagulant device 20 in a fixed (stable) position within the blood coagulant container 15.

As seen in FIG. 2, the coagulant layer 54 of the tapered upper portion 11 is only in contact with the inner surfaces 17, 21 of the blood coagulant container 15 at a ledge (flange) section 36, and the top section (distal end) 16 of the device 20 inserted into the shoulder 46 of the container 15. This results in a minimum contact of the device 20 with the inner surfaces 17, 21 of the container 15 while maintaining the blood coagulant device 20 in the fixed relation to the container 15.

Returning to FIG. 1, the subject blood coagulant device 20 includes a handle member 13 with both a handle lower section (proximal portion) 13B and a handle upper section (distal portion) 13A formed in a one piece (integral) formation. As is seen, both handle lower section 13B and handle upper section 13A include the through opening (channel) 14 passing through handle member 13 in an axial direction 32.

A blood coagulant mechanism 12' is provided in the subject device 20. It is secured to an outer surface 33 of the handle upper section 13A and to the ledge section 36 of the handle member 13 and extends radially with respect to the axial direction 32 at a location where the handle lower section 13B and the handle upper section 13A connect.

The blood coagulant mechanism 12' includes the tapered sponge-like upper portion 11 formed by an elastic composition layer 52 secured to the outer surface 33 of the handle upper section (distal portion) 13A, and the blood coagulant composition layer 54 which is secured to an outer surface of the elastic composition layer 52 to form the combined one piece blood coagulation mechanism 12'. The elastic composition layer 52 may be adhered to the outer surface 33 of the handle upper section 13A by epoxy, glue, heat welding, or some like technique to fixedly secure the elastic composition layer 52 to the handle upper section 13A to prevent displacement therebetween. Similarly, the coagulant layer 54 is adhered to the elastic composition layer 52 through a coating process to fixedly secure the coagulant layer 54 impregnated with the blood clotting medicine 12 to the elastic composition layer 52.

Shown in FIGS. 1-3, the combined blood coagulation mechanism 12' is cross-sectionally depicted as having a substantially linearly tapered contour from the flange section 36 of the handle member 13 to a top surface 38 of the combined coagulant mechanism 12' (at the distal end 16 of the device 20). The elastic composition layer 52 may be formed of a sponge-like material which allows elasticity for insertion into the nose of a patient experiencing a nose bleed. The elastic composition layer 52 may be formed of a flexible plastic, rubber material, or other like composition, which permits flexibility of the elastic composition layer 52.

The tapering contour of the elastic composition layer 52 allows for insertion into the nostrils of patients which would have varying internal contours dependent upon individual patients. In this manner, blood coagulant device 20 can be easily inserted into nostrils of different opening sizes dependent upon a particular patient's anatomy.

Referring again to FIGS. 1-3, the blood coagulant device 20 has the top surface 38 at the distal end 16 which is arcuately formed to be further detailed in following paragraphs. Additionally, the lower section 13B of the handle 13 member includes an arcuately formed lower surface 40 at the proximal end 18 of the device 20 for interfacing in secure contact with the blood coagulant container 15 to be further described and seen in FIGS. 2 and 3.

The blood coagulant layer 54 is formed on (secured to) the outer surface of the elastic composition layer 52. The layer 54 is generally formed of, or impregnated with, a composition selected from the group of chitosan, aluminum chloride-6-hydrate (ACH drug), or some like drug composition, which has the blood clotting properties.

The handle member 13 (in both the handle lower section 13B and upper section 13A) is formed from a material selected from the group of a closed cell plastic composition or other rigid material which can be grasped by the fingers of a patient.

As seen in FIG. 2, the blood coagulant assembly 10 also includes the blood coagulant container 15 which is formed by the container upper section 15T and the container lower section 15B which, when joined each to the other, form a container chamber 42 contoured with the internal surfaces 17, 21 for insert, placement and fixed securement of the blood coagulant device 20 within the blood coagulant container 15 prior to the removal and use of the blood coagulant device 20 by the patient.

The container upper section 15T may be threadedly secured to the container lower section 15B in a releasable securement with a threadingly engagement mechanism 44. Alternatively, the container upper section 15T may be releasably secured to the lower section 15B of the container 15 by frictional securement engagement therebetween. The important consideration being that the container upper section 15T be easily and quickly removed from the container lower section 15B when the user experiences a bleeding nose episode.

Referring again to FIG. 2, the blood coagulant container 15 includes a shoulder section 46 for frictionally engaging the upper side surface 47 of the blood coagulant device 20 in a fixed location. Further, the container lower section 15B includes a lower arcuately contoured internal surface 50 for matingly engaging the arcuately contoured upper surface 38 of blood coagulant device 20. In this manner, there is an increased surface area for maintaining the blood coagulant device 20 in a fixed relation to the lower surface 50 of the blood coagulant container 15.

Further, the lower handle section 13B having the lower arcuate surface 40 at the proximal end 18 of the device 20 is mounted contiguous with the container top interior surface 21 for further stably maintaining the blood coagulant device 20 within the container 15.

In this manner, the blood coagulant device 20 is maintained in a substantially rigid manner within the blood coagulant container 15 prior to the removal of the blood coagulant device 20 from the container 15. This is important due to the fact that the blood coagulant assembly 10 is generally maintained in a pocket, or purse, or other pouch, which will result in movement and displacement of the blood coagulant device 20 within the container 15 and may result in an abrasion of the coagulant layer 54 impregnated with the drug 12 prior to its use. The axial distance between the lower arcuate contoured surface 50 of the container 15 and the top interior surface 21 of the container 15 is substantially equal to the axial length of the blood coagulant device 20 to further insure a snuggled fixed positioning of the blood coagulant device 20 within the container 15.

As seen in FIGS. 2-4, the blood coagulant container 15 is initially joined in one piece formation by coupling the container top section 15T to the container bottom section 15B, for example, through a threadingly engaging mechanism 44. When needed, the mechanism 44 is deactivated, and the container top section 15T is removed from the container bottom section 15B. The blood coagulant device 20 is subsequently removed from the container chamber 42, and the blood coagulant device 20 lower section 13B is grasped by the fingers 27 of the patient. The blood coagulant device 20 is subsequently inserted, as depicted in FIG. 4, into a nostril of the nose 25 of the patient to form a contiguous engagement between the medicine impregnated layer 54 with the inner surface inside the nostril of the patient for contacting the fractured vein (ulcerations) and coagulating the blood.

One of the important aspects of the subject assembly 10 is that the handle 13 is formed from a rigid material. The distal portion 13A of the handle member 13 extends internally the entire length of the tapered sponge-like upper portion 11, and thus reinforces the otherwise elastic layers 52, 54 to prevent an unwanted deformation and deviation of the coagulant layer 54 from a contiguous contact with the inner surface of the nostril when the device 20 is inserted into the nostril.

The rigidness of the proximal portion 13B of the handle 13 is also important for providing a secure grip for the user's fingers in insertion into and removal of the device 10 from the nostril.

Various other modifications, adaptations and alternative designs are of course possible in light of the teachings as presented herein. Therefore, it should be understood that while still remaining within the scope and meaning of the appended claims, this invention could be practiced in a manner other than that which is specifically described herein.

What is claimed is:

1. A blood coagulant assembly comprising:
   a) a blood coagulant device adapted to be reversibly insertable into a nostril of a patient having a nose bleed, said blood coagulant device having a handle member configured with a handle lower section and a handle upper section formed in a one piece formation, and a ledge section formed at a joint of said lower and upper handle sections, said handle upper section having an outer surface, wherein said handle lower and upper sections are configured with an opening passing therethrough in an axial direction; wherein the opening communicates between the outer surface of the handle upper section and an outer surface of the handle lower section
   b) a blood coagulant device container having a container top section and a container lower section secured to and releasable each from the other for maintaining said blood coagulant device in a fixed location within said blood coagulant device container prior to removal of said blood coagulant device from said blood coagulant container; and
   c) a blood coagulant mechanism secured to said outer surface of said handle upper section and to said ledge section of said handle member extending radially at a location between said handle lower and upper sections, said blood coagulant mechanism having an elastic composition layer secured to said outer surface of said handle upper section with a blood coagulant composition layer secured to an outer surface of said elastic composition layer to form a one piece combined blood coagulant mechanism, and a blood coagulant medicinal composition at least partially impregnating said blood coagulant composition layer, said combined blood coagulant mechanism having a substantially linearly tapered contour extending from said ledge section of said handle member to a top surface of said combined blood coagulant mechanism, wherein said top surface of said combined coagulant mechanism is arcuately formed.

2. The assembly as recited in claim 1, where said handle member lower section includes an arcuately formed lower surface.

3. The assembly as recited in claim 2, where an axial distance between said lower arcuately contoured surface of the handle member lower section and said interior upper surface of said blood coagulant device container is substantially equal to an axial length of said blood coagulant device when said upper and lower sections of said blood coagulant device container are joined each to the other.

4. The assembly as recited in claim 1, where said blood coagulant medicinal composition is selected from the group consisting of chitosan, aluminum chloride-6-hydrate, and combinations thereof.

5. The assembly as recited in claim 1, where said handle member is formed of a material selected from the group of a closed cell plastic composition or rigid material.

6. The assembly as recited in claim 5, wherein said rigid handle upper section reinforces said elastic composition layer and blood coagulant composition layer.

7. The assembly as recited in claim 1, where said container upper section and said container lower section, being joined to each other, form a container chamber for insert and storage of said blood coagulant device in a stable position.

8. The assembly as recited in claim 7, where said container upper section is threadedly secured to said container lower section.

9. The assembly as recited in claim 7, where said container upper section is releasably secured to said container lower section by a functional securement therebetween.

10. The assembly as recited in claim 1, where said container lower section includes an internal shoulder section for frictionally engaging a side surface of said blood coagulant device.

11. The assembly as recited in claim 10, where said container lower section includes a lower arcuately contoured internal surface for matingly engaging an arcuately contoured upper surface of said blood coagulant device.

12. The assembly as recited in claim 11, where said container upper section includes an interior upper surface contiguous with a lower surface of said handle member when said blood coagulant device is mounted in said blood coagulant device container.

* * * * *